United States Patent
Koseoglu et al.

(10) Patent No.: US 10,048,194 B2
(45) Date of Patent: Aug. 14, 2018

(54) CHARACTERIZATION OF CRUDE OIL BY ULTRAVIOLET VISIBLE SPECTROSCOPY

(71) Applicant: Saudi Arabian Oil Company, Dhahran (SA)

(72) Inventors: Omer Refa Koseoglu, Dhahran (SA); Adnan Al-Hajji, Dhahran (SA); Gordon Jamieson, London (GB)

(73) Assignee: Saudi Arabian Oil Company, Dhahran (SA)

(*) Notice: Subject to any disclaimer, the term of this patent is extended or adjusted under 35 U.S.C. 154(b) by 248 days.

(21) Appl. No.: 15/060,230

(22) Filed: Mar. 3, 2016

(65) Prior Publication Data

US 2016/0187253 A1    Jun. 30, 2016

Related U.S. Application Data

(63) Continuation-in-part of application No. PCT/US2016/012144, filed on Jan. 5, 2016, which is a continuation-in-part of application No. 13/400,865, filed on Feb. 21, 2012, now Pat. No. 9,285,307.

(60) Provisional application No. 62/099,723, filed on Jan. 5, 2015.

(51) Int. Cl.
*G06F 19/00* (2011.01)
*G01N 21/33* (2006.01)
*G01N 33/28* (2006.01)

(52) U.S. Cl.
CPC .............. *G01N 21/33* (2013.01); *G01N 33/28* (2013.01); *G01N 33/2811* (2013.01); *G01N 2201/12* (2013.01)

(58) Field of Classification Search
CPC ....... A61K 31/353; Y02E 50/16; C12P 19/02; B01J 19/08
USPC ................................ 702/25, 13, 14, 182–185
See application file for complete search history.

(56) References Cited

U.S. PATENT DOCUMENTS

| | | |
|---|---|---|
| 4,251,870 A | 2/1981 | Jaffe |
| 4,971,915 A | 11/1990 | Schwartz et al. |
| 5,223,714 A | 6/1993 | Maggard |
| 5,452,232 A | 9/1995 | Espinosa et al. |
| 5,490,085 A | 2/1996 | Lambert et al. |
| 5,572,030 A | 11/1996 | Ranson et al. |
| 5,600,134 A | 2/1997 | Ashe et al. |
| 5,602,755 A | 2/1997 | Ashe et al. |
| 5,656,810 A | 8/1997 | Alfano et al. |
| 5,699,269 A | 12/1997 | Ashe et al. |

(Continued)

FOREIGN PATENT DOCUMENTS

| | | |
|---|---|---|
| CA | 2781273 A1 | 12/2013 |
| EP | 0305090 A2 | 8/1988 |

(Continued)

OTHER PUBLICATIONS

Birch, C., Oil & Gas Journal, Jan. 14, 2002, pp. 54-59.

(Continued)

*Primary Examiner* — Edward Raymond
(74) *Attorney, Agent, or Firm* — Abelman, Frayne & Schwab

(57) ABSTRACT

A system and a method for calculating and assigning an indicative value, such as cetane number, pour point, cloud point and aniline point, of a fraction of an oil sample based on an index calculated and assigned from ultraviolet visible spectroscopy data of the oil sample.

40 Claims, 3 Drawing Sheets

(56) References Cited

U.S. PATENT DOCUMENTS

| | | | |
|---|---|---|---|
| 6,258,987 B1 | 7/2001 | Schmidt et al. | |
| 6,602,403 B1 | 8/2003 | Steffens et al. | |
| 6,711,532 B1 | 3/2004 | Spieksma | |
| 6,841,779 B1 | 1/2005 | Roehner et al. | |
| 8,930,149 B1 | 1/2015 | Koseoglu | |
| 2002/0052769 A1 | 5/2002 | Navani et al. | |
| 2003/0141459 A1 | 7/2003 | Hegazi et al. | |
| 2003/0195708 A1 | 10/2003 | Brown | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0040051 A1 | 2/2008 | Franklin et al. | |
| 2008/0248967 A1 | 10/2008 | Butler et al. | |
| 2008/0260584 A1 | 10/2008 | Gudde et al. | |
| 2010/0113311 A1 | 5/2010 | Eccleston et al. | |
| 2010/0211329 A1 | 8/2010 | Farquharson et al. | |
| 2011/0152136 A1 | 6/2011 | Hughes et al. | |
| 2013/0118734 A1* | 5/2013 | Csutak | E21B 47/102 166/264 |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106029 A1 | 4/2015 | Koseoglu et al. | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0984277 A1 | 3/2000 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Pavlovic, K., Oil & Gas Journal, Nov. 22, 1999, pp. 51-56.

Coen, Duvekot, Fast Analysis of Paraffins, iso-Paraffins, Olefins, iso-Olefins, Naphthenes and Aromatics in Hydrocarbon Streams, Varian, Inc., pp. 1-4.

ASTM D2887-01, Standard Test Method for Boiling Range Distribution of Petroleum Fractions by Gas Chromatography, Annual Book of ASTM Standards, vol. 14, No. 02, pp. 204-216.

Hidajat, K, et al., Quality characterisation of crude oils by partial least square calibration of NIR spectral profiles, Near Infrared Spectrosc, vol. 8, pp. 53-59.

Falla, F, et al., Characterization of crude petroleum by NIR, Journal of Petroleum Science and Engineering, vol. 51, 2006, pp. 127-137.

Terra, L. et al., Petroleomics by electrospray ionization FT-ICR mass spectrometry coupled to partial least squares with variable selection methods: prediction of the total acid number of crude oils, Analyst, vol. 139, 2014, pp. 4908-4916.

Pereira, Thieres M. C., An evaluation of the aromaticity of asphaltenes using atmospheric pressure photoionization Fourier transform ion cyclotron resonance mass spectrometry—APP (±) FT-ICR MS, Fuel, vol. 118, 2014, pp. 348-357.

Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.

Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.

Adhvaryu, A et al., Quantitative NMR Spectroscopy for the Prediction of Base Oil Properties, Tribology Transactions, vol. 43, No. 2, pp. 245-250.

Shea, T.M., Modeling Base Oil Properties using NMR Spectroscopy and Neural Networks, Tribology Transactions, vol. 46, No. 3, 2003, pp. 296-302.

Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.

Hasan, M.U. et al., Structural characterization of Saudi Arabian heavy crude oil by n.m.r. spectroscopy, Fuel, vol. 62, 1983, pp. 518-523.

Seetar, G, et al., Cetana Number Predictions of a Trial Index Based on Compositional Analysis, American Chemical Society, 1989, pp. 308-312.

Cookson, D.J. et al., Investigation of the Chemical Basis of Diesel Fuel Properties, Energy & Fuels, vol. 2, No. 6, 1988, pp. 854-860.

Patra, D, et al, Determination of Synchronous Fluorescence Scan Parameters for Certain Petroleum Products, Journal of Scientific & Industrial Research, Apr. 1, 2000, pp. 300-305.

Khanmohammadi, M, et al., Characterization of petroleum-based products by infrared spectroscopyu and chemometrics, Trac Trends in Analytical Chem, vol. 35, 2012.

Kok, M, et al., High pressure TGA analysis of crude oils, Thermochimica Acta., vol. 287, No. 1, Sep. 1, 1996, pp. 91-99.

PCT/US2016/012144, International Search Report and Written Opinion dated May 13, 2016, 18 pages.

* cited by examiner

CHARACTERIZATION OF CRUDE OIL BY ULTRAVIOLET VISIBLE SPECTROSCOPY

RELATED APPLICATIONS

This application
is a continuation-in-Part under 35 USC § 365(c) of PCT Patent Application No. PCT/US 16/12144 filed Jan. 5, 2016, which claims the benefit of priority under 35 USC § 119(e) to U.S. Provisional Patent Application No. 62/099,723 filed Jan. 5, 2015, and
is a continuation-in-part of U.S. patent application Ser. No. 13/400,865 filed Feb. 21, 2012, the disclosures of which are all hereby incorporated by reference.

FIELD OF THE INVENTION

This invention relates to a method and process for the evaluation of samples of crude oil and its fractions by ultraviolet visible spectroscopy.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°–180° C.), kerosene (180°–240° C.), gas oil (240°–370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°–520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two phases separate is recorded as the aniline point or mixed aniline point.

To determine these properties of gas oil or naphtha fractions conventionally, these fractions have to be distilled off from the crude oil and then measured/determined using various analytical methods that are laborious, costly and time consuming.

In the field of organic chemistry, UV-visible spectrophotometry, which deals with electronic transitions within molecules, has traditionally provided unique information about aromatic and heteroaromatic compounds which absorb strongly in the UV region (200 nm-400 nm). Despite this and owing to the complex molecular nature of crude oil, UV-visible spectra of these oils are often described as featureless, poorly defined spectra.

New rapid and direct methods to help better understand crude oil composition and properties from the analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining one or more indicative properties of crude oil samples are provided. Indicative properties (e.g., cetane number, pour point, cloud point and aniline point) of a gas oil fraction in crude oil samples are assigned as a function of density and data derived from ultraviolet visible spectroscopy measurement of the crude oil samples. The correlations also provide information about the gas oil properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings, in which.

DETAILED DESCRIPTION OF INVENTION

A system and method is provided for determining one or more indicative properties of a hydrocarbon sample. Indicative properties (e.g., cetane number, pour point, cloud point and aniline point) of a gas oil fraction in crude oil samples are assigned as a function of data obtained from ultraviolet visible spectroscopy data of a crude oil sample and the density of the crude oil sample.

The correlations provide information about gas oil and/or naphtha indicative properties without fractionation/distillation (crude oil assays) and will help producers, refiners, and marketers to benchmark the oil quality and, as a result, valuate the oils without performing the customary extensive and time-consuming crude oil assays. The currently used crude oil assay method is costly in terms of money and time. It costs about $50,000 US and takes two months to complete one assay. With the method and system herein, the crude oil can be classified as a function of NMR data, and thus decisions can be made for purchasing and/or processing.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction. Samples can be obtained from various sources, including an oil well, stabilizer, extractor, or distillation tower.

In the system and method herein, spectra are obtained by a suitable known or to be developed UV-visible spectrophotometry techniques UV-visible spectrophotometry is carried out on a sample of crude oil according to the method and system herein to provide unique information about aromatic and heteroaromatic compounds which absorb strongly in the UV region (200 nm-400 nm). Specific individual aromatic compounds and components have maxima at well-defined wavelengths. Wavelength maxima of known aromatic compounds and components are evaluated and extracted from the UV spectra of crude oils. These maxima are used to formulate indices for the aromatic content of the crude oil. These indices are used to assign one or more indicative properties of the oil, e.g., cetane number, pour point, cloud point and aniline point. Importantly, this information can be obtained relatively rapidly and inexpensively from a UV-visible scan as compared to the prior art assay methods described above.

Figure 1:
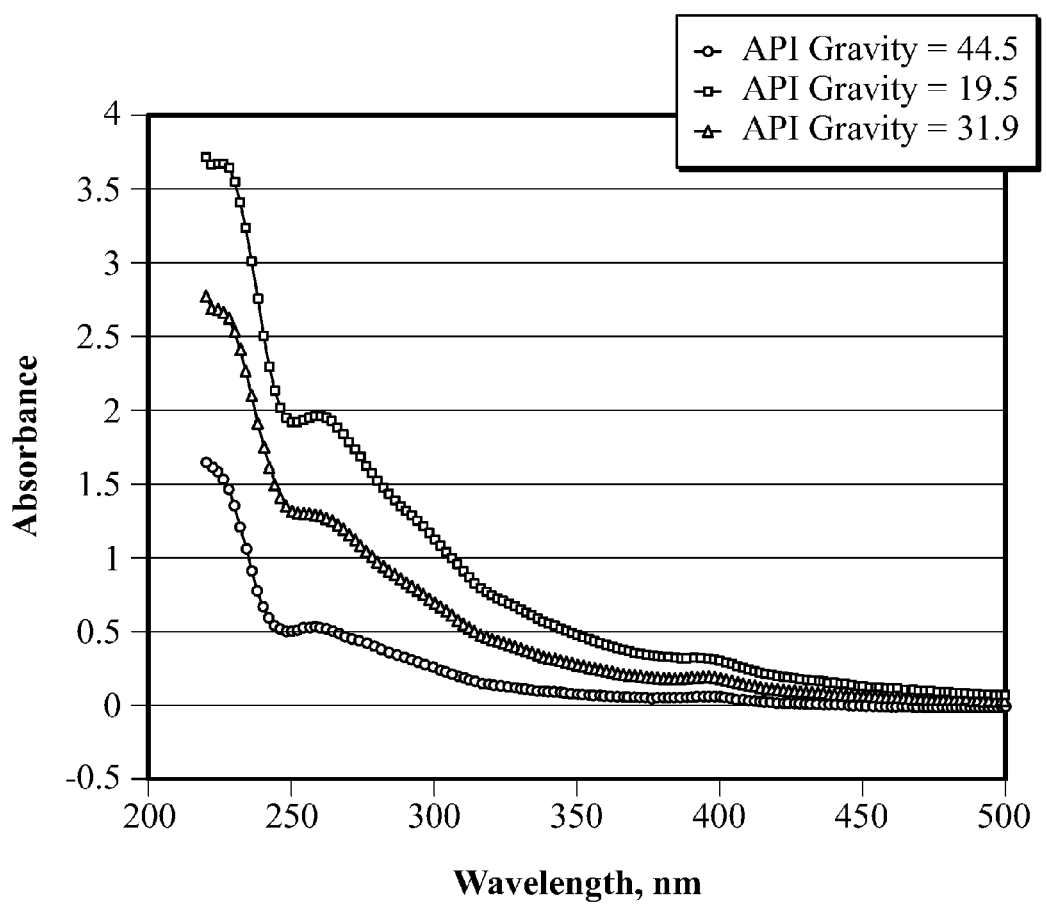
FIG. 1 is a graphic plot of typical ultraviolet visible spectroscopy data for three types of a crude oil sample solution prepared as described below.
Figure 2:
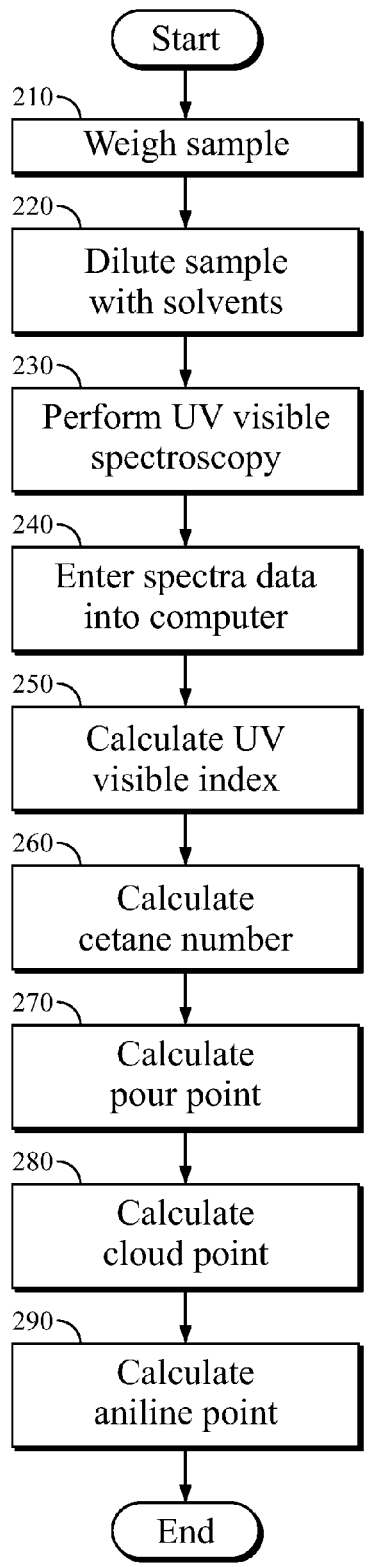
FIG. 2 is a process flow diagram of steps carried out to establish a value for indicative properties of a gas oil fraction, using the system and method herein.

FIG. 2 shows a process flowchart in a method according to one embodiment herein. Crude oil samples are prepared and analyzed by ultraviolet visible spectrophotometry between 200-500 nm, in certain embodiments between 220-400 nm. In step 210, a crude oil sample is weighed.

In step 220, solutions are prepared by dissolving a sample of the crude oil in a two-part solvent system of a paraffinic solvent having from 5-20 carbon atoms and a polar solvent, e.g., at a ratio of 90:10% v/v. In certain embodiments, effective paraffinic solvents include iso-octane. In certain embodiments, effective polar solvents include dichloromethane.

The use of a polar solvent prevents precipitation of asphaltenes from the crude oil sample and ensures that all solutions are translucent for the measurement. The polar solvents are selected based on their Hildebrand solubility factors or their two-dimensional solubility parameters. The overall Hildebrand solubility factor is a well known measure of polarity and has been calculated for numerous compounds. See, for example, the Journal of Paint Technology, Vol. 39, No. 505 (February 1967). The solvents can also be described by their two-dimensional solubility parameter. See, for example, I. A. Wiehe, "Polygon Mapping with Two-Dimensional Solubility Parameters", *I&EC Research*, 34, 661-673 (1995). The complexing solubility parameter component, which describes the hydrogen bonding and electron donor-acceptor interactions, measures the interaction energy that requires a specific orientation between an atom of one molecule and a second atom of a different molecule. The field force solubility parameter, which describes the van der Waals and dipole interactions, measures the interaction energy of the liquid that is not destroyed by changes in the orientation of the molecules.

The UV absorbance of the crude oil solutions is determined, for instance, in a conventional one cm quartz cell. The absorbance values of the samples are summed at predetermined increments (e.g., even numbers, odd number, or increments of any number) between a predetermined range, e.g., between 200-500 nm, in certain embodiments between 220-400 nm to calculate the characterization index.

In step 230, one or more samples of crude oil in dilute solution are analyzed by UV-visible spectrophotometry over the wavelengths 200-500 nm, in certain embodiments 220-400 nm.

In step 240, the density and spectra data are entered into a computer. In step 250, the CUVISI is calculated.

Equation (1) shows a crude oil ultraviolet visible index, CUVISI.

$$CUVISI = \sum_{i=L}^{H} (Absorbance_{(Ni-220)}/x^*10); \qquad (1)$$

where:
Absorbance=absorbance value of the prepared crude oil sample solution at a specific wavelength over the range L to H at intervals of N, whereby in certain embodiments L is between about 200 nm and 220 nm and H is between 400 nm and 500 nm, and N is between 1 and 3, and x is the weight of the sample used, in mg.

Figure 3:
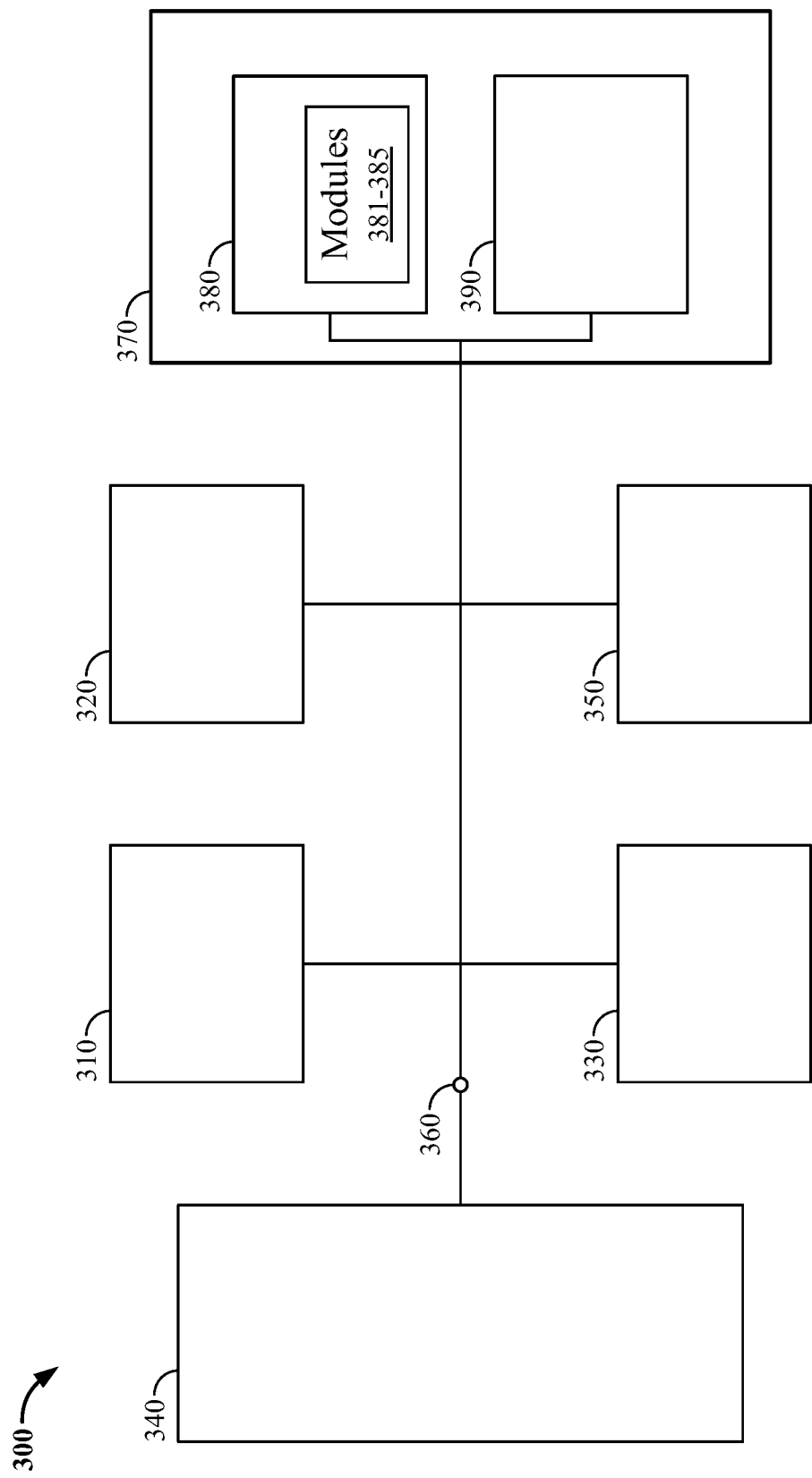
FIG. 3 is a block diagram of components of a system for implementing the invention according to one embodiment.

Equations (2) through (5) show, respectively, the cetane number, pour point, cloud point and aniline point of gas oils boiling in the range 180-370° C. that can be predicted from the density and ultraviolet visible spectroscopy index (CUVISI) of crude oils. In step 260, the cetane number is calculated. In step 270, the pour point is calculated. In step 280, the cloud point is calculated. In step 290, the aniline point is calculated. While FIG. 2 shows steps 260 through 290 performed sequentially, they can be performed in any order, and in certain embodiments fewer than all can be calculated and assigned.

$$\text{Cetane Number (CET)}=K_{CET}+X1_{CET}*\text{DEN}+X2_{CET}*\text{DEN}^2+X3_{CET}*\text{DEN}^3+X4_{CET}*(\text{CUVISI}/100)+X5_{CET}*(\text{CUVISI}/100)^2+X6_{CET}*(\text{CUVISI}/100)^3+X7_{CET}*\text{DEN}*(\text{CUVISI}/100) \qquad (2);$$

$$\text{Pour Point (PP)}=K_{PP}+X1_{PP}*\text{DEN}+X2_{PP}*\text{DEN}^2+X3_{PP}*\text{DEN}^3+X4_{PP}*(\text{CUVISI}/100)+X5_{PP}*(\text{CUVISI}/100)^2+X6_{PP}*(\text{CUVISI}/100)^3+X7_{PP}*\text{DEN}*(\text{CUVISI}/100) \qquad (3);$$

$$\text{Cloud Point (CP)}=K_{CP}+X1_{AP}*\text{DEN}+X2_{CP}*\text{DEN}^2+X3_{CP}*\text{DEN}^3+X4_{CP}*(\text{CUVISI}/100)+X5_{CP}*(\text{CUVISI}/100)^2+X6_{CP}*(\text{CUVISI}/100)^3+X7_{CP}*\text{DEN}*(\text{CUVISI}/100) \qquad (4);$$

$$\text{Aniline Point (AP)}=K_{AP}+X1_{AP}*\text{DEN}+X2_{AP}*\text{DEN}^2+X3_{AP}*\text{DEN}^3+X4_{AP}*(\text{CUVISI}/100)+X5_{AP}*(\text{CUVISI}/100)^2+X6_{AP}*(\text{CUVISI}/100)^3+X7_{AP}*\text{DEN}*(\text{CUVISI}/100) \qquad (5);$$

where:
DEN=density of the crude oil sample;
CUVISI=crude oil UV visible index;
and $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, and $X1_{AP}$-$X7_{AP}$ are constants that were developed using linear regression techniques, An exemplary block diagram of a computer system 300 by which indicative property calculation modules can be implemented is shown in FIG. 3. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores a crude oil UV visible index (CUVISI) calculation module 381 and one or more indicative property calculation modules 382-385 such as a cetane number calculation module 382, a pour point calculation module 383, a cloud point calculation module 384, and an aniline point calculation module 385. Data storage memory 390 stores data used and/or generated by the one or more modules of the present invention, including but not limited to density of the crude oil sample, UV absorbance data or portions thereof used by the one or more modules of the present system, and calculated indicative properties generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

Computer system 300 preferably supports an operating system, for example stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

EXAMPLE

Exemplary constants $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, and $X1_{AP}$-$X7_{AP}$ were developed using linear regression techniques and are given in Table 3:

TABLE 3

| Property | Cetane Number (CET) | Pour Point (PP) | Cloud Point (CP) | Aniline Point (AP) |
|---|---|---|---|---|
| K | −472522.2 | −551951.6 | −72809.6 | −168599.5 |
| X1 | 1629297.3 | 1914678.7 | 253698.1 | 553283.7 |
| X2 | 1858806.6 | −2198029.9 | −291533.9 | −598770.2 |
| X3 | 707220.4 | 842964.0 | 112071.8 | 213228.6 |
| X4 | −13648.8 | −15981.5 | −3122.3 | −4138.5 |
| X5 | 17763.9 | 24751.5 | 4976.9 | −562.7 |
| X6 | −7241.0 | −10000.1 | −2006.9 | 239.6 |
| X7 | −656.8 | −4616.8 | −1040.9 | 5250.3 |

The instrument is allowed to warm up for 30 minutes prior to analysis and is auto-zeroed without cells in both sample and reference beams. The reference cell is filled with the solvent mixture then placed in the reference beam. Solutions of the crude oil sample solutions prepared as described above are successively placed in a clean quartz sample cell and the spectra are recorded against the reference solvent blank. The spectra are recorded at a scan speed of 100 nm/min with a fast response time.

A sample of Arabian medium crude with a density of 0.8828 Kg/l was analyzed by UV-Visible spectroscopy. The spectra data, normalized to 10 mg/L, is shown in Table 4:

TABLE 4

| Wave Length | Absor., nm |
|---|---|
| 220 | 2.9442 |
| 222 | 2.8301 |
| 224 | 2.8296 |
| 226 | 2.8382 |
| 228 | 2.8341 |
| 230 | 2.8014 |
| 232 | 2.7397 |
| 234 | 2.6512 |
| 236 | 2.5278 |
| 238 | 2.3901 |
| 240 | 2.2547 |
| 242 | 2.1199 |
| 244 | 1.9885 |
| 246 | 1.8776 |
| 248 | 1.7951 |
| 250 | 1.7386 |
| 252 | 1.7024 |
| 254 | 1.6845 |
| 256 | 1.6781 |
| 258 | 1.6789 |
| 260 | 1.6737 |
| 262 | 1.6580 |
| 264 | 1.6311 |
| 266 | 1.5994 |
| 268 | 1.5665 |
| 270 | 1.5242 |
| 272 | 1.4714 |
| 274 | 1.4128 |
| 276 | 1.3549 |
| 278 | 1.3037 |
| 280 | 1.2559 |
| 282 | 1.2120 |
| 284 | 1.1722 |
| 286 | 1.1353 |
| 288 | 1.1002 |
| 290 | 1.0706 |
| 292 | 1.0416 |
| 294 | 1.0107 |
| 296 | 0.9769 |
| 298 | 0.9436 |
| 300 | 0.9194 |
| 302 | 0.9003 |
| 304 | 0.8711 |
| 306 | 0.8393 |
| 308 | 0.8026 |
| 310 | 0.7688 |
| 312 | 0.7390 |

TABLE 4-continued

| Wave Length | Absor., nm |
|---|---|
| 314 | 0.7111 |
| 316 | 0.6869 |
| 318 | 0.6640 |
| 320 | 0.6436 |
| 322 | 0.6252 |
| 324 | 0.6074 |
| 326 | 0.5912 |
| 328 | 0.5746 |
| 330 | 0.5561 |
| 332 | 0.5368 |
| 334 | 0.5175 |
| 336 | 0.4980 |
| 338 | 0.4781 |
| 340 | 0.4590 |
| 342 | 0.4454 |
| 344 | 0.4302 |
| 346 | 0.4162 |
| 348 | 0.4042 |
| 350 | 0.3910 |
| 352 | 0.3786 |
| 354 | 0.3650 |
| 356 | 0.3525 |
| 358 | 0.3407 |
| 360 | 0.3288 |
| 362 | 0.3173 |
| 364 | 0.3069 |
| 366 | 0.2963 |
| 368 | 0.2870 |
| 370 | 0.2787 |
| 372 | 0.2711 |
| 374 | 0.2642 |
| 376 | 0.2574 |
| 378 | 0.2524 |
| 380 | 0.2468 |
| 382 | 0.2425 |
| 384 | 0.2394 |
| 386 | 0.2371 |
| 388 | 0.2359 |
| 390 | 0.2360 |
| 392 | 0.2351 |
| 394 | 0.2342 |
| 396 | 0.2314 |
| 398 | 0.2258 |
| 400 | 0.2174 |

Equation (1) is applied and the data recorded in Table 4 for the sample of Arab medium crude oil produces a CUVISI of 94.9748.

Applying equation (2) and the constants from Table 3, $$\text{Cetane Number (CET)} = K_{CET} + X1_{CET}*\text{DEN} + X2_{CET}*\text{DEN}^2 + X3_{CET}*\text{DEN}^3 + X4_{CET}*(\text{CUVISI}/100) + X5_{CET}*(\text{CUVISI}/100)^2 + X6_{CET}*(\text{CUVISI}/100)^3 + X7_{CET}*\text{DEN}*(\text{CUVISI}/100) = (-472522.2) + (1629297.3)(0.8828) + (1858806.6)(0.8828)^2 + (707220.4)(0.8828)^3 + (-13648.8)(94.9748/100) + (17763.9)(94.9748/100)^2 + (-7241.0)(94.9748/100)^3 + (-656.8)(0.8828)(94.9748/100) = 59$$

Applying equation (3) and the constants from Table 3, $$\text{Pour Point (PP)} = K_{PP} + X1_{PP}*\text{DEN} + X2_{PP}*\text{DEN}^2 + X3_{PP}*\text{DEN}^3 + X4_{PP}*(\text{CUVISI}/100) + X5_{PP}*(\text{CUVISI}/100)^2 + X6_{PP}*(\text{CUVISI}/100)^3 + X7_{PP}*\text{DEN}*(\text{CUVISI}/100) = (-551951.6) + (1914678.7)(0.8828) + (-2198029.9)(0.8828)^2 + (842964.0)(0.8828)^3 + (-15981.5)(94.9748/100) + (24751.5)(94.9748/100)^2 + (-10000.1)(94.9748/100)^3 + (-4616.8)(0.8828)(94.9748/100) = -9° \text{ C.}$$

Applying equation (4) and the constants from Table 3, $$\text{Cloud Point (CP)} = K_{CP} + X1_{CP}*\text{DEN} + X2_{CP}*\text{DEN}^2 + X3_{CP}*\text{DEN}^3 + X4_{CP}*(\text{CUVISI}/100) + X5_{CP}*(\text{CUVISI}/100)^2 + X6_{CP}*(\text{CUVISI}/100)^3 + X7_{CP}*\text{DEN}*(\text{CUVISI}/100) = (-72809.6) + (253698.1)(0.8828) + (-291533.9)(0.8828)^2 + (112071.8)(0.8828)^3 + (-3122.3)(94.9748/100) + (4976.9)(94.9748/100)^2 + (-2006.9)(94.9748/100)^3 + (-1040.9)(0.8828)(94.9748/100) = -11° \text{ C.}$$

Applying equation (5) and the constants from Table 3, $$\text{Aniline Point (AP)} = K_{AP} + X1_{AP}*\text{DEN} + X2_{AP}*\text{DEN}^2 + X3_{AP}*\text{DEN}^3 + X4_{AP}*(\text{CUVISI}/100) + X5_{AP}*(\text{CUVISI}/100)^2 + X6_{AP}*(\text{CUVISI}/100)^3 + X7_{AP}*\text{DEN}*(\text{CUVISI}/100) = (-168599.5) + (553283.7)(0.8828) + (-598770.2)(0.8828)^2 + (213228.6)(0.8828)^3 + (-4138.5)(94.9748/100) + (-562.7)(94.9748/100)^2 + (239.6)(94.9748/100)^3 + (5250.3)(0.8828)(94.9748/100) = 66° \text{ C.}$$

Accordingly, as shown in the above example, indicative properties including cetane number, pour point, cloud point and aniline point can be assigned to the crude oil samples without fractionation/distillation (crude oil assays).

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 USPQ2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

We claim:

1. A system for assigning an indicative property to a fraction of an oil sample based upon ultraviolet visible spectroscopy data, the system comprising:
a non-volatile memory device that stores calculation modules and data, the data including ultraviolet visible spectroscopy data indicative of absorbance values at predetermined increments between a predetermined range for the oil sample;
a processor coupled to the memory;

a first calculation module that calculates a crude oil ultraviolet visible index value of the fraction from the sample's weight and the absorbance values of the spectroscopy data;

a second calculation module that calculates and assigns the indicative property for the fraction of the crude oil as a function of the ultraviolet visible index and density of the oil sample.

2. The system as in claim 1 wherein the oil sample is crude oil.

3. The system as in claim 1 wherein the oil sample is obtained from an oil well, stabilizer, extractor, or distillation tower.

4. The system as in claim 1 wherein the indicative property is a cetane number.

5. The system as in claim 1 wherein the indicative property is a pour point.

6. The system as in claim 1 wherein the indicative property is a cloud point.

7. The system as in claim 1 wherein the indicative property is an aniline point.

8. The system as in claim 1, wherein the first calculation module calculates and assigns the ultraviolet visible index with a summation of the absorbance values over the range of wavelengths, divided by the weight of the sample.

9. The system as in claim 1 wherein the second calculation module calculates and assigns the indicative property with a multi-variable polynomial equation with a set of predetermined constant coefficients developed using linear regression wherein the variables are the ultraviolet visible index and the density of the oil sample.

10. The system as in claim 1, wherein
the first calculation module calculates and assigns the ultraviolet visible index with a summation of the absorbance values over the range of wavelengths, divided by the weight of the sample, and
the second calculation module calculates and assigns the indicative property with a multi-variable polynomial equation with a set of predetermined constant coefficients developed using linear regression wherein the variables are the ultraviolet visible index and the density of the oil sample.

11. A system for assigning an indicative property to a fraction of an oil sample comprising:
an ultraviolet spectrometer that outputs ultraviolet visible spectroscopy data;
a non-volatile memory device that stores calculation modules and data, the data including ultraviolet visible spectroscopy data indicative of absorbance values at predetermined increments between a predetermined range for the oil sample;
a processor coupled to the memory;
a first calculation module that calculates a crude oil ultraviolet visible index value of the fraction from the sample's weight and the absorbance values of the spectroscopy data;
a second calculation module that calculates and assigns the indicative property for the fraction of the crude oil as a function of the ultraviolet visible index and density of the oil sample.

12. The system as in claim 11, wherein the first calculation module calculates and assigns the ultraviolet visible index with a summation of the absorbance values over the range of wavelengths, divided by the weight of the sample.

13. The system as in claim 11. wherein
the first calculation module calculates and assigns the ultraviolet visible index with a summation of the absorbance values over the range of wavelengths, divided by the weight of the sample, and
the second calculation module calculates and assigns the indicative property with a multi-variable polynomial equation with a set of predetermined constant coefficients developed using linear regression wherein the variables are the ultraviolet visible index and the density of the oil sample.

14. A method for operating a computer to assign an indicative property to a fraction of an oil sample based upon ultraviolet visible spectroscopy data, the method comprising:
entering into the computer ultraviolet visible spectroscopy data indicative of absorbance values at predetermined increments between a predetermined range for the oil sample;
calculating and assigning a crude oil ultraviolet visible index value of the fraction from the sample's weight and the absorbance values of the spectroscopy data; and
calculating and assigning the indicative property of a gas oil fraction as a function of the ultraviolet visible index and density of the oil sample.

15. The method as in claim 14 wherein the oil sample is crude oil.

16. The method as in claim 3 wherein the oil sample is obtained from an oil well, stabilizer, extractor, or distillation tower.

17. The method as in claim 14 wherein the indicative property is a cetane number.

18. The method as in claim 14 wherein the indicative property is a pour point.

19. The method as in claim 14 wherein the indicative property is a cloud point.

20. The method as in claim 14 wherein the indicative property is an aniline point.

21. The method as in claim 14 wherein plural indicative properties are calculated including at least two indicative properties selected from the group consisting of cetane number, pour point, cloud point and aniline point.

22. The method as in claim 14 wherein the indicative property is of a gas oil fraction boiling in the nominal range 180-370° C.

23. The method as in claim 14 wherein the ultraviolet visible spectroscopy data is obtained from an ultraviolet visible spectroscopy analysis in a wavelength range from 220-400 nm.

24. The method of claim 14, wherein the ultraviolet visible index is calculated and assigned by summation of the absorbance values over the range of wavelengths, divided by the weight of the sample.

25. The system as in claim 14, wherein the second calculation module calculates and assigns the indicative property with a multi-variable polynomial equation with a set of predetermined constant coefficients developed using linear regression wherein the variables are the ultraviolet visible index and the density of the oil sample.

26. The method as in claim 14, wherein the indicative property is calculated and assigned with a multi-variable polynomial equation with a set of predetermined constant coefficients developed using linear regression wherein the variables are the ultraviolet visible index and the density of the oil sample.

27. The method of claim 14, wherein
the ultraviolet visible index is calculated and assigned by summation of the absorbance values over the range of wavelengths, divided by the weight of the sample, and the indicative property is calculated and assigned with a multi-variable polynomial equation with a set of predetermined constant coefficients developed using linear regression wherein the variables are the ultraviolet visible index and the density of the oil sample.

28. A method for assigning an indicative property to a fraction of an oil sample comprising:
obtaining ultraviolet visible spectroscopy data indicative of absorbance values at predetermined increments between a predetermined range for the oil sample;
entering into a computer the obtained ultraviolet visible spectroscopy data;
calculating and assigning a crude oil ultraviolet visible index value of the fraction from the sample's weight and the absorbance values of the spectroscopy data; and
calculating and assigning the indicative property of a gas oil fraction as a function of the ultraviolet visible index and density of the oil sample.

29. The method of claim 28, further comprising preparing the sample for ultraviolet visible spectroscopy analysis by diluting the sample with a solvent mixture of paraffinic and polar solvents.

30. The method of claim 29, wherein the paraffinic solvent contains from 5-20 carbon atoms.

31. The method of claim 29, wherein the polar solvent is selected based on is Hildebrand solubility factor or by its two-dimensional solubility parameter.

32. The method of claim 31, wherein the polar solvent has a Hildebrand solubility rating of at least 19.

33. The method of claim 31, wherein the two-dimensional solubility factors of the polar solvent are the complexing solubility parameter and the field force solubility parameter.

34. The method of claim 33, wherein the polar solvent's complexing solubility parameter component describes the hydrogen bonding and electron donor acceptor interactions.

35. The method of claim 33, wherein the polar solvent's field force solubility parameter is based on the van der Waals and dipole interactions.

36. The method of claim 29, wherein the paraffinic-to-polar solvent ratio is 70:30 or greater.

37. The method of claim 29, wherein the paraffinic-to-polar solvent ratio is 90:10 or greater.

38. The method of claim 28, wherein the ultraviolet visible index is calculated and assigned by summation of the absorbance values over the range of wavelengths, divided by the weight of the sample.

39. The method as in claim 28, wherein the indicative property is calculated and assigned with a multi-variable polynomial equation with a set of predetermined constant coefficients developed using linear regression wherein the variables are the ultraviolet visible index and the density of the oil sample.

40. The method of claim 28, wherein
the ultraviolet visible index is calculated and assigned by summation of the absorbance values over the range of wavelengths, divided by the weight of the sample, and
the indicative property is calculated and assigned with a multi-variable polynomial equation with a set of predetermined constant coefficients developed using linear regression wherein the variables are the ultraviolet visible index and the density of the oil sample.

* * * * *